United States Patent
Iddan

(10) Patent No.: US 9,042,963 B2
(45) Date of Patent: May 26, 2015

(54) SYSTEM AND METHOD FOR ACQUIRING IMAGES FROM WITHIN A TISSUE

(71) Applicant: GIVEN IMAGING LTD., Yoqneam (IL)

(72) Inventor: Gavriel J. Iddan, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 206 days.

(21) Appl. No.: 13/737,324

(22) Filed: Jan. 9, 2013

(65) Prior Publication Data
US 2013/0178735 A1   Jul. 11, 2013

Related U.S. Application Data

(60) Provisional application No. 61/584,330, filed on Jan. 9, 2012, provisional application No. 61/640,023, filed on Apr. 30, 2012.

(51) Int. Cl.
*A61B 5/00* (2006.01)
*A61B 6/02* (2006.01)
*G02B 13/22* (2006.01)

(52) U.S. Cl.
CPC .............. *A61B 5/0066* (2013.01); *A61B 6/02* (2013.01); *G02B 13/22* (2013.01)

(58) Field of Classification Search
USPC .......................................... 600/425, 473, 476
See application file for complete search history.

(56) References Cited

U.S. PATENT DOCUMENTS

| 5,024,529 | A | * | 6/1991 | Svetkoff et al. | 356/608 |
| 5,465,147 | A | | 11/1995 | Swanson | |
| 6,124,930 | A | | 9/2000 | Fercher | |
| 2007/0263226 | A1 | * | 11/2007 | Kurtz et al. | 356/492 |

OTHER PUBLICATIONS

Schuman, Joel S. "Spectral Domain Optical Coherence Tomography for Glaucoma (An AOS Thesis)". Trans Am Ophthalmol Soc, vol. 106, 2008, pp. 426-458.*
B. Bourquin, P. Seitz and R.P. Salathe "Optical coherence topography based on a two-dimensional smart detector array" Optics Letters/ vol. 26, No. 8/ Apr. 15, 2001.
G. Hausler & M. W. Lindner "Coherent Radar" J. of Biomed Optics 3(1), Jan. 1998.

* cited by examiner

*Primary Examiner* — Unsu Jung
*Assistant Examiner* — Phong K Huynh
(74) *Attorney, Agent, or Firm* — Pearl Cohen Zedek Latzer Baratz LLP

(57) ABSTRACT

Systems and methods for imaging within depth layers of a tissue include illuminating light rays at different changing wavelengths (frequencies), collimating illuminated light rays using a collimator, and splitting light rays using a beam splitter, such that some of the light rays are directed towards a reference mirror and some of the rays are directed towards the tissue. The systems and methods further include reflecting light rays from the reference mirror towards the imager, filtering out non-collimated light rays reflected off the tissue by using a telecentric optical system, and reflecting collimated light rays reflected off the tissue towards the imager, thus creating an image of an interference pattern based on collimated light rays reflected off the tissue and off the reference mirror. The method may further include creating full 2D images from the interference pattern for each depth layer of the tissue using Fast Fourier transform.

15 Claims, 11 Drawing Sheets

$R_{ij}(k) = FFT\{S_{ij}\}$

Reflectivity layers
Rij(k) in the x (depth) direction.

Resulting from the FFT applied on a sequence of illumination wavelengths per pixel [i,j]

SYSTEM AND METHOD FOR ACQUIRING IMAGES FROM WITHIN A TISSUE

CROSS-REFERENCE TO RELATED APPLICATIONS

This application claims the benefit of U.S. Provisional Patent Application Ser. No. 61/584,330, filed Jan. 9, 2012, and of U.S. Provisional Patent Application Ser. No. 61/640,023, filed Apr. 30, 2012, which are hereby incorporated by reference in their entireties.

FIELD OF THE INVENTION

The present invention relates to the field of imaging. In particular, the present invention relates to a system and method for acquiring images from within deep layers of a tissue.

BACKGROUND OF THE INVENTION

Optical Coherence Tomography (OCT) is used to capture micrometer-resolution, two-dimensional images from within optical scattering media, for example, a biological tissue. OCT employs relatively long wavelength light, e.g., near-infrared light, which penetrates into the scattering media. In recent years, OCT has emerged as a very useful diagnostic tool and is extensively used in ophthalmology. Efforts are under way to extend the OCT method to other diagnostic needs such as dermatology, cardiology and the list is constantly growing.

Generating a full two-dimensional image of layers within a tissue, without the need for transverse scanning with a single point at a time is highly desirable, yet the methods currently proposed are associated with high noise level due to scattered light arriving to the imager.

SUMMARY OF THE INVENTION

The main deficiency of current devices that incorporate OCT, as described above, is e.g., low signal to noise ratio due to stray reflections that reach the imager. In order to overcome at least this deficiency, the present invention presents systems and method that comprise an illumination source with a large illumination beam area (such that there is congruence between the field of illumination and the field of view), which eliminates the need for transverse scanning, since substantially the entire image is captured in one illumination session. These systems further filter out non-collimated light reflections. Other systems and method according to the present invention include illuminating with large illumination beam area, filtering out non-collimated light reflections and using Fourier transform for processing the images acquired by the system and displaying the images so as to illustrate the depth layers of the tissue. These systems and method using Fourier transform make the need for moving scanning elements within the OCT system redundant.

The present invention is intended to filter out from the imaged object, e.g., tissue, the non-collimated light reflections generated as scattered light rays. These non-collimated light rays are not contributing any useful information, since they lost their directivity and coherence. By not carrying any information they are a source of noise, which degrades the image.

Eliminating the unwanted light rays is achieved by adding a telecentric lens system in the optical path of the light rays reflected from the tissue target. The telecentric optics has a unique property of enabling only parallel light rays that are also perpendicular to the tissue target, to pass through them. Thus, when a telecentric optical system is added to the return path of light rays reflected from the tissue target, the telecentric optics prevents the scattered light rays from arriving to the detector, thereby resulting in enhanced performance of the OCT.

In addition, in some embodiments, instead of moving some elements of the system, e.g., the mirror, and instead of moving the tissue specimen being imaged, a tunable light source that may illuminate in variable frequencies, e.g., a monochromator, or a tunable laser, is used as part of the system. The tunable light source illuminates in changing monochromatic illumination frequencies, which are later translated to the different layers of the tissue.

Following image acquisition per each illumination frequency, a method for displaying the acquired images includes a preceding step of processing the images. The processing step includes applying Fast Fourier Transform (FFT) per pixel of the imager for the entire illumination frequencies/wavelengths illuminated onto the tissue. That is, the FFT is applied per an imager's pixel in all of the acquired images, each of the images acquired following illumination of a different monochromatic wavelength. The FFT transforms the illumination frequencies per pixel to depth of tissue layers per pixel. All pixels of the imager related to the same tissue layer are combined in order to create one full two-dimensional image. The same process is done per each tissue layer (following the FFT), thus a full set of two-dimensional images per every tissue layer is obtained. One possible image display includes displaying the images side by side, beginning with the most superficial layer on the left and ending with the deepest layer on the right, or vice versa. Another display includes creating a collage or a tessellation of the images. Another possible display includes overlaying the images one on top of the other, so as to create a 3D image of the tissue. An operator could select a section of the 3D image that seems suspicious for expressing pathologies, e.g., a polyp, and examine that section along the entire tissue layers, thereby being able to better assess the tissue condition.

BRIEF DESCRIPTION OF THE DRAWINGS

The present invention will be understood and appreciated more fully from the following detailed description taken in conjunction with the appended drawings in which.

Figure 1:
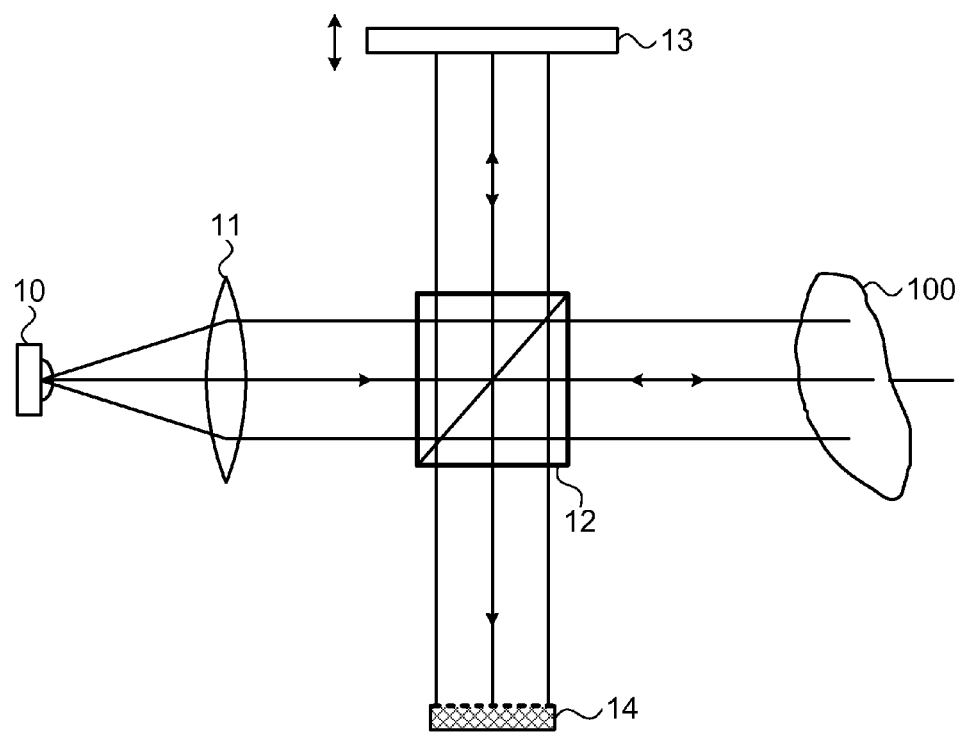
FIG. 1 is a schematic illustration of a full field OCT system, in accordance with the prior art.

It will be appreciated that, for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

The systems and methods described in the present invention may provide acquisition of images from different layers within a tissue target, which may enable performing an optical biopsy of the tissue target. Images acquired from different layers of a tissue may teach on tissue characteristics. The images acquired from within the tissue may be compared with, for example, cancerous tissue, in order to assess condition of the imaged tissue, e.g., whether the tissue is a healthy tissue or one that suffers from cancer or pre-cancer conditions.

Reference is now made to FIG. 1, which schematically illustrates a full field OCT system according to the prior art. A Full-field OCT system, in accordance with the prior art, comprises an illumination source 10 for illuminating a tissue target. Illumination source 10 typically illuminates in relatively long wavelength light, e.g., near-infrared light, which penetrates into inner layers of a tissue target. The well-known OCT system further comprises a collimator 11 for collimating the illuminated light rays. The collimated light rays pass through a beam splitter 12, which splits the light rays; some of the collimated light rays are directed towards a reference mirror 13 and some of the collimated light rays are directed towards an examined tissue 100. The light rays that reach the reference mirror 13 are then reflected off it towards imager 14, through beam splitter 12. The light rays that reach the examined tissue 100 are reflected off the tissue 100 in all directions, and are then directed towards the imager 14 by beam splitter 12. The layer from which the light rays are reflected off is determined when comparing the rays reflected off the tissue 100 to the rays reflected off the reference mirror 13. The reference mirror 13 may be a moveable mirror, thus images of different layers from different depths along the inside of the tissue 100 may be acquired.

In some embodiments, the beam splitter 12, reference mirror 13, and imager 14 may compose an interferometer, e.g., a Michelson interferometer.

Figure 2:
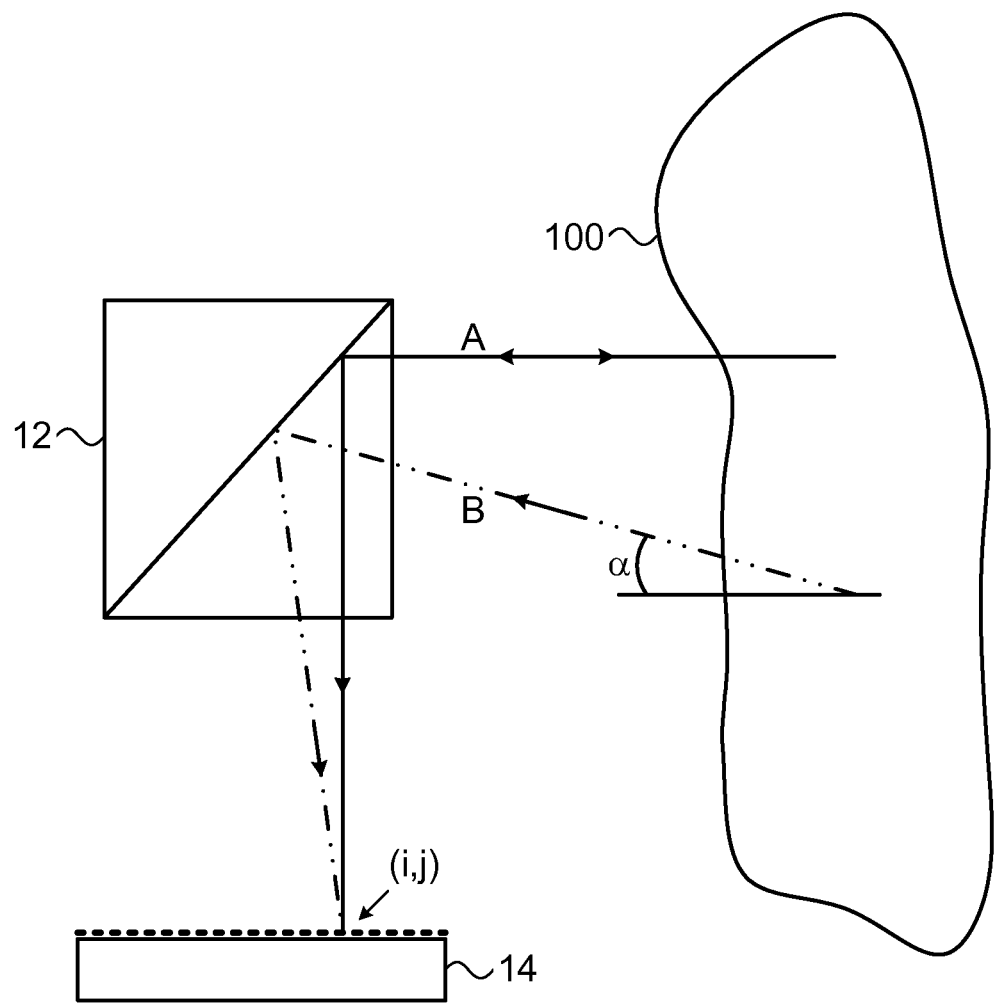
FIG. 2 is a schematic illustration of light rays reflections in an OCT system, in accordance with the prior art.

Reference is now made to FIG. 2, which schematically illustrates light rays reflections in an OCT system, in accordance with the prior art. Light rays are reflected off the tissue in all directions; however, only one certain direction of reflected light rays is the one that provides information regarding the tissue's condition. The direction of reflected light rays that provides information on tissue condition is the direction that is parallel to the collimated light rays and which is perpendicular to the beam splitter 12. FIG. 2 illustrates direction of two examples of light rays reflected off the examined tissue 100. Light ray A, which is reflected off tissue 100, is reflected in a direction parallel to the collimated illuminated light rays. Light ray A is one of many parallel light rays that are used to create an image from within the tissue, and which determines tissue condition. Light ray A is an example of a ray reflected from a single point of interest in tissue 100, which correlates to a ray reflected off reference mirror 13 (see FIG. 1). The ray from the tissue and the ray from the reference mirror create an image of an interference pattern. When the ray from the tissue is reflected from the point of interest of the tissue, the ray from the tissue and the ray from the reference mirror undergo constructive interference, and thus a signal would be collected by imager 14 (FIG. 1) at pixel [i,j].

Light ray B, which is reflected off tissue 100, is reflected in a direction that is not parallel to the collimated illuminated light rays. Light ray B is reflected from a different point in tissue 100, unrelated to the point from which ray A is reflected. Light ray B is shifted in an angle α compared to the direction of reflection of light ray A or to the direction of collimated illuminated light rays. Light ray B, which is not parallel to the collimated illuminated light rays should not be used to create the image and thereby determine tissue condition, since it lost its directivity and coherence. By not carrying any information, light rays that are similar to light ray B, are a source of noise, which degrades the image. Thus, light ray B should be prevented from reaching pixel [i,j] of imager 14.

Figure 3:
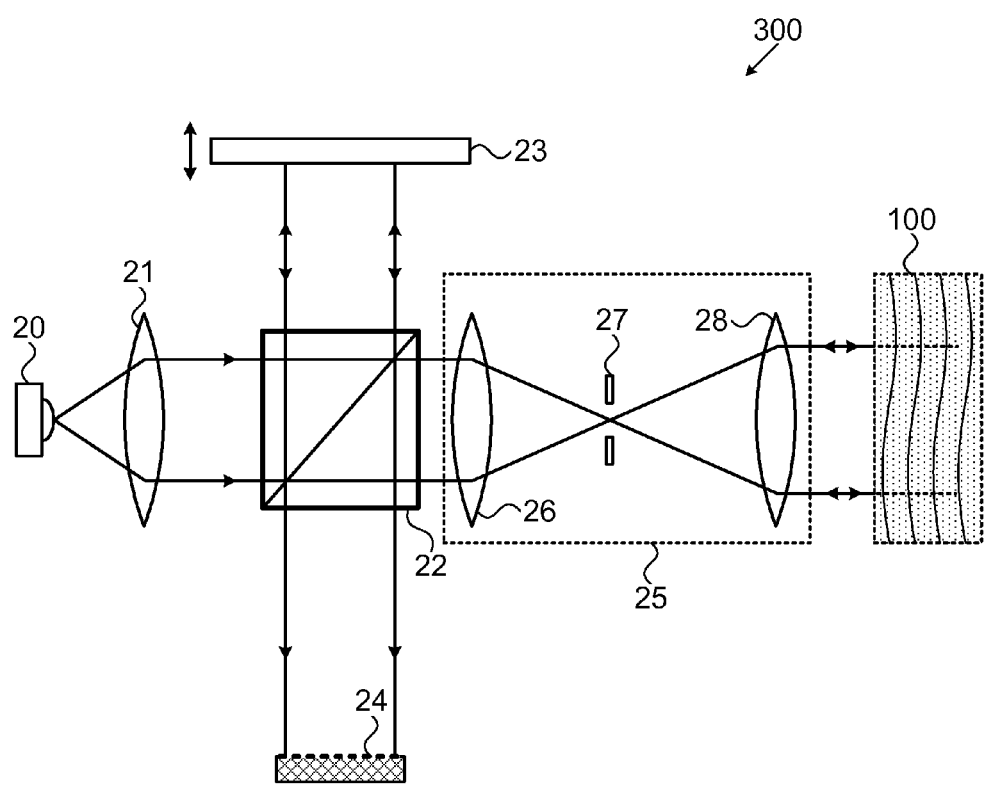
FIG. 3 is a schematic illustration of a full-field OCT system for acquiring images from within a tissue, in accordance with one embodiment of the present invention.

In order to overcome the deficiencies of OCT systems as disclosed in the prior art and as explained above, which include low signal to noise ratio, the present invention provides a new OCT system, which includes a telecentric optical system, and a new processing method. Reference is now made to FIG. 3, which illustrates a schematic full-field OCT system 300 for acquiring images from within a tissue, in accordance with one embodiment of the present invention. The OCT system 300 disclosed in FIG. 3 may comprise illumination source 20. Illumination source 20 may typically illuminate in relatively long wavelength light, e.g., near-infrared light, which penetrates into inner layers of a tissue target. Illumination source 20 may be any of the following: an IR LED, a Super Luminescence Diode (SLD), an Incandescence light source, or any other light source that may illuminate IR light. Illuminations source 20 may be designed such to create a relatively large illumination beam area compared to that of illumination sources used in prior art OCT systems, which create a thin single pixel pencil beam. For example, the illumination beam area may be 1 mm$^2$ or 5 mm$^2$, though other sizes of the beam may be possible. The illumination beam area is large such that there is congruence between the field of illumination (FOI) and the field of view (FOV). Thus, OCT system 300 eliminates the need for transverse scanning that is required in prior art systems, since in one illumination session of system 300, the entire image is captured.

The OCT system 300 further comprises a collimator 21, which collimates the illuminated light rays irradiated by illumination source 20. The collimated light rays are then split by beam splitter 22; some of the collimated light rays may be directed towards reference mirror 23, which may be a moveable mirror (as described in FIG. 1), and some of the collimated rays may be directed towards the tissue target 100. Since reference mirror 23 is moveable, it enables scanning along the deep layers of tissue 100, i.e., along z axis. The light rays that reach moveable reference mirror 23 may be reflected off it towards imager 24, through beam splitter 22, as in OCT systems of the prior art. Imager 24 may be any imager that is sensitive in the short or NIR range, e.g., a CCD imager without IR blocking filter, CMOS imager without IR blocking filter, InGaAs (indium-Galium-Arsenide) imager and a band pass (BP) filter, Bolometric imager with a proper BP filter, or InSb (indium-Tin) imager with BP filter.

In some embodiments, beam splitter 22, moveable reference mirror 23, and imager 24 may compose an interferometer, e.g., a Michelson interferometer (as described in FIG. 1). Furthermore, OCT system 300 may comprise a telecentric optical system 25.

Telecentric optical system 25 may be located between the beam splitter 22 and the tissue target 100. In some embodiments, telecentric optical system 25 may comprise a collimating/condensing lens 26, an aperture 27 and condensing/collimating lens 28. Before light rays that are reflected off the tissue, reach imager 24, they pass through telecentric optical system 25. The light rays reflected off the tissue pass through condensing/collimating lens 28, which condenses the light rays and enables some of them to pass through aperture 27. The rays that passed through aperture 27 may then pass through collimating/condensing lens 26, which filters the light rays such that only originally collimated light rays pass through collimating/condensing lens 26, while the rest of the rays do not pass through collimating/condensing lens 26. The result is that only originally collimated light that was reflected by the tissue reaches imager 24, thus substantially no noise reaches imager 24.

In some embodiments, telecentric optical system 25 may be located between beam splitter 22 and imager 24 instead of between beam splitter 22 and tissue target 100. Either of these locations of telecentric optical system 25 may create the same effect of eliminating noise from reaching the imager, by enabling only collimated light reflected by tissue 100 to reach imager 24.

In some embodiments, the optical axes of moveable reference mirror 23 and imager 24 may be perpendicular to the optical axis of collimated light from illumination source 20 and to collimated light reflected off the tissue 100.

An image of an interference pattern may be created by imager 24. Collimated light rays reflected off reference mirror 23, and collimated light rays reflected off the tissue target create the interference pattern. The interference pattern is for a certain depth layer of the tissue. According to some embodiments, the interference pattern may be used to determine the depth of the tissue from which the light rays were reflected off. In some embodiments, the interference image created by the light rays reflected off the tissue and off the reference mirror may further be compared to images of tissue with various pathologies, which were acquired and analyzed prior to the present imaging session, in order to determine whether the imaged tissue suffers from any of the pathologies.

According to some embodiments, the system in FIG. 3 may further comprise a processor which may generate slices or a complete three-dimensional view of the tissue target, from said interference patterns generated by the imager, using known methods.

Figure 4:
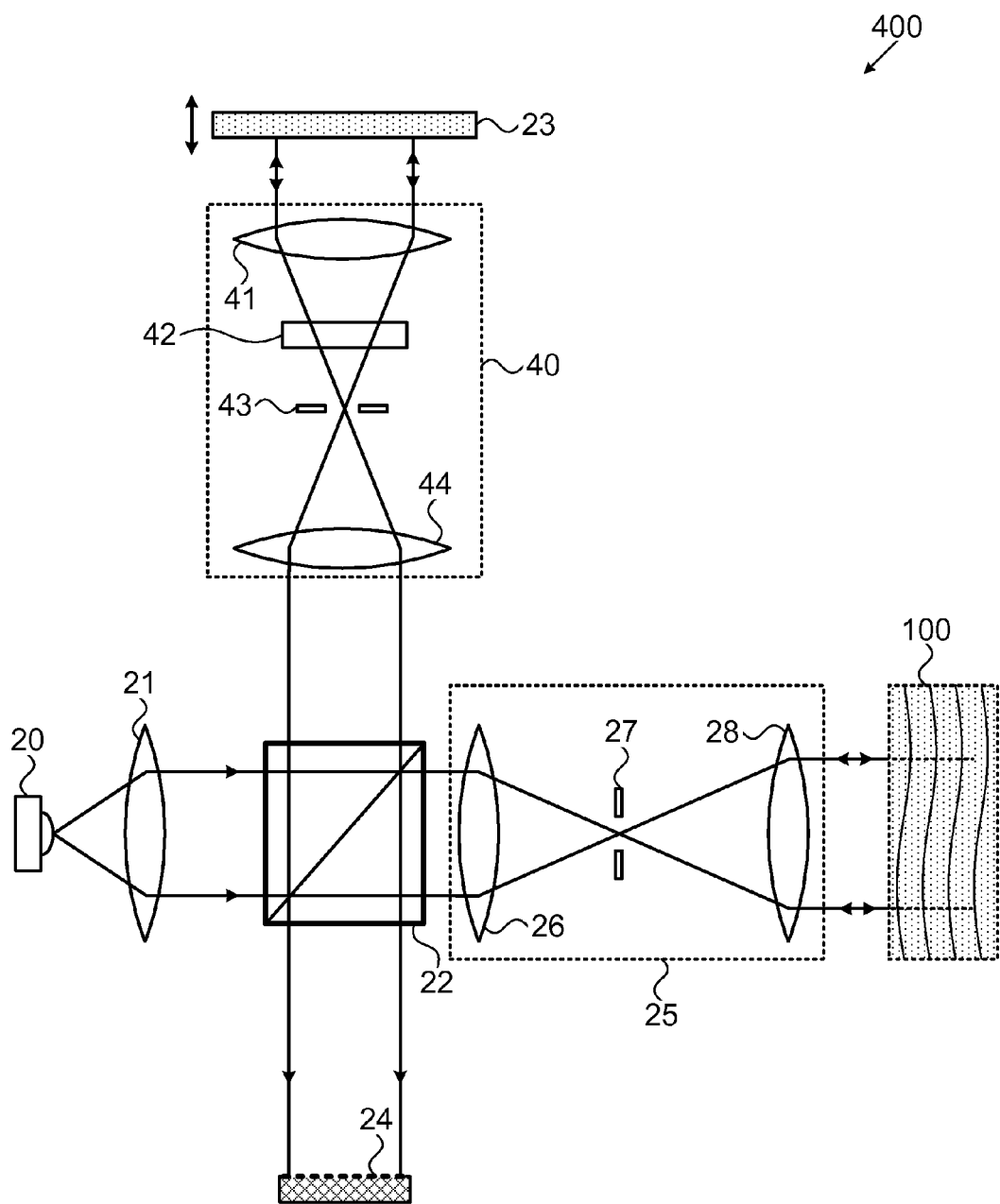
FIG. 4 is a schematic illustration of a full-field OCT system for acquiring images from within a tissue, in accordance with a second embodiment of the present invention.

Reference is now made to FIG. 4, which schematically illustrates a full-field OCT system 400 for acquiring images from within a tissue, in accordance with a second embodiment of the present invention. The OCT system 400 in FIG. 4 comprises a first telecentric optical system 25, as in system 300 of FIG. 3 and a second telecentric optical system 40. This second telecentric optical system 40 may be located between moveable reference mirror 23 and beam splitter 22. Telecentric optical system 40 may comprise an arrangement of lenses, e.g., condensing/collimating lens 41, a shutter 43, and a collimating/condensing lens 44.

Since telecentric optical system 25 decreases the amount of light rays reflected off the tissue and which reach the imager by filtering out non-collimated light rays, the intensity of light rays detected from tissue 100 by imager 24 is quite low. Therefore, in order to enable imager 24 to create an image from the light rays reflected off tissue 100, the illumination source 20 should typically be of high intensity. A high intensity illumination source 20 may cause light rays reflected off moveable reference mirror 23 to be of high intensity as well. When the intensity of light reflected off moveable reference mirror 23 is higher than the intensity of light reflected off the tissue, too much flux is captured by imager 24, which creates noise. Thus, comparing the intensity of collimated light rays reflected by tissue 100 to the intensity of collimated light rays reflected by moveable reference mirror 23 is difficult. The intensity of collimated light rays reflected by reference mirror 23 should be of the same order as the intensity of collimated light rays reflected by tissue 100, in order to enable optimal operation of imager 24.

Therefore, telecentric optical system 40 may be used in order to decrease the amount of light that is reflected off reference mirror 23, thus decrease the intensity of light reflected off reference mirror 23. According to some embodiments, light rays reflected off reference mirror 23 may pass through condensing/collimating lens 41, and may then pass through shutter 43. Shutter 43 may limit the amount of rays that pass through, thus decreasing the intensity of light reflected off mirror 23. The light rays that did pass through shutter 43 may then pass through collimating/condensing lens 44 in order to resemble to the direction of initially illuminated collimated light rays, and thus serve as a reference (of both intensity and direction) to the collimated light rays reflected off the tissue target 100.

According to some embodiments, shutter 43 may be changeable, such that it may be synchronized with the changing tissue depth from which images are acquired. Reference mirror 23 may be a moveable mirror, in order to enable image acquisition from various depths within the tissue. The deeper the layer is within the tissue, the less light rays reflected off the tissue reach the imager 24. Therefore, shutter 43 should be adjusted according to the depth within the tissue from which images are acquired. The deeper the layer is, the smaller the opening of shutter 43 is, and vice versa. In some embodiments, movement of the reference mirror 23, as well as changing of the opening/closure of shutter 43 may be manually performed by an operator of the OCT system 400. In other embodiments, the movement of reference mirror 23 and the synchronized opening/closure of shutter 43 may be performed automatically such that images of various depths are acquired one after the other. The amount of movement of reference mirror 23 and thus amount of opening/closure of shutter 43 may be preset by the operator of OCT system 400 according to embodiments of the present invention.

In some embodiments, telecentric optical system 40 may comprise a neutral density filter 42, which may be located between condensing/collimating lens 41 and collimating/condensing lens 44. Neutral density filter 42 may replace, or be added to shutter 43. Neutral density filter 42 may be a variable uniform density filter, which may decrease the intensity of light reflected off the reference mirror 23. In some embodiments, a set of discrete filters may be used so that a desired filter is positioned between condensing/collimating lens 41 and collimating/condensing lens 44. The filters may be synchronously changed with moveable reference mirror 23 and thus decrease the intensity of light reflected off mirror 23 in the appropriate amount that corresponds to the intensity of light reflected off tissue target 100. For example, the set of filters may be arranged on a wheel turnable in a plane perpendicular to the optical axis of telecentric optical system 25 so that a desired filter may be positioned in the path of light between condensing/collimating lens 41 and collimating/condensing lens 44.

In other embodiments, reducing the intensity of illumination of light reflected off reference mirror 23 may be achieved by incorporating into the system a non-symmetrical beam splitter, instead of beam splitter 22. A non-symmetrical beam splitter may deliver towards the reference mirror 23 only a fraction of the illumination that is delivered towards the tissue.

Figure 5:
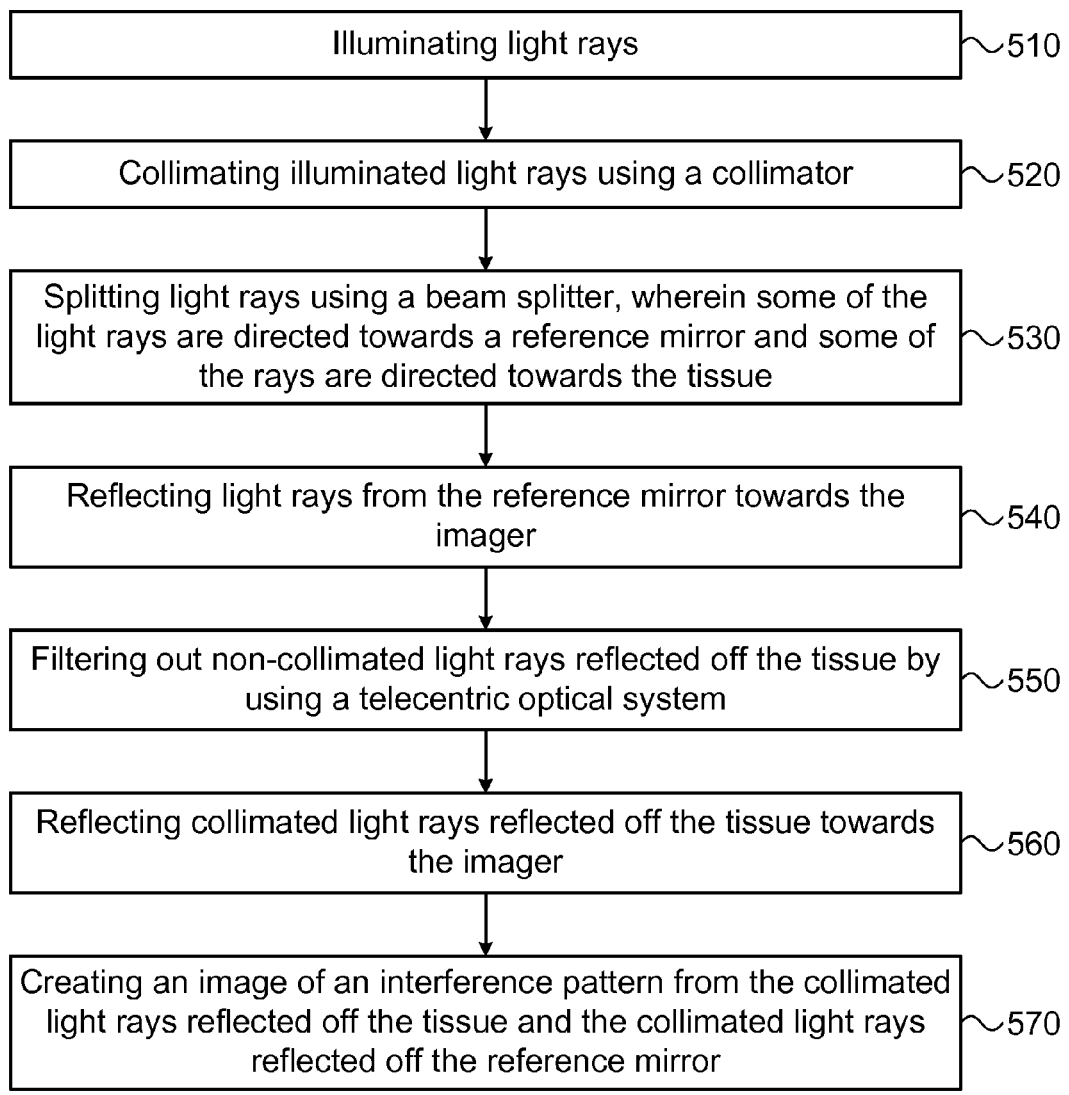
FIG. 5 is a flow chart illustrating a method for acquiring images from within a tissue, in accordance with embodiments of the present invention.

Reference is now made to FIG. 5, which illustrates a flow chart of a method for acquiring images from within depth layers of a tissue, in accordance with embodiments of the present invention. The method may comprise the following steps:

illuminating light rays (510);
  collimating illuminated light rays using a collimator (520);
  splitting light rays using a beam splitter, wherein some of the light rays are directed towards a reference mirror and some of the rays are directed towards the tissue, while both portions of light rays preserve their collimated nature1 (530);
  reflecting light rays from the reference mirror towards the imager (540);
  filtering out non-collimated light rays reflected off the tissue by using a telecentric optical system (550);
  reflecting collimated light rays reflected off the tissue towards the imager (560);
  creating an image of an interference pattern from the collimated light rays reflected off the tissue and the collimated light rays reflected off the reference mirror (570).

The image of interference pattern is created by a mix of collimated light rays reflected off the reference mirror and collimated light rays reflected off the tissue. If the ray reflected off the tissue does not originate from a point of interest in the tissue, the ray reflected off the tissue and the corresponding ray reflected off the reference mirror undergo destructive interference, thus no signal is detected by pixel [i,j] of the imager. However, if the ray reflected off the tissue does originate from a point of interest in the tissue, the ray reflected off the tissue and the corresponding ray reflected off the reference mirror undergo constructive interference, thus a signal is detected by pixel [i,j] of the imager.

In some embodiments, the method may further comprise the step of moving the reference mirror in order to obtain images of various depths/layers from within the tissue. This step may be performed prior to the step of illuminating light rays (510), and may be repeated as desired by the operator, or may be preset according to embodiments of the present invention.

According to some embodiments, the method may further comprise the step of decreasing intensity of light reflected off the reference mirror (synchronously with movement of reference mirror) by using a second telecentric optical system that includes a density filter, said step performed prior to reflecting light rays from the reference mirror towards the imager (540).

The method may further comprise the step of creating an image of an interference pattern for each depth layer, from the collimated light rays reflected off each of the tissue layers.

In some embodiments, the method may further comprise the step of comparing the interference image to images of various pathological tissues. Comparison between the acquired images and various pathologies may enable assessment of the tissue target's condition, e.g., whether the tissue comprises any of the reference pathologies or whether the imaged tissue is healthy.

In the following embodiments, the present invention provides a new OCT system without any moving elements (e.g., a moveable reference mirror as in FIG. 3), which includes a telecentric optical system, and a new processing method, which eliminates the need for any moveable elements.

Figure 6:
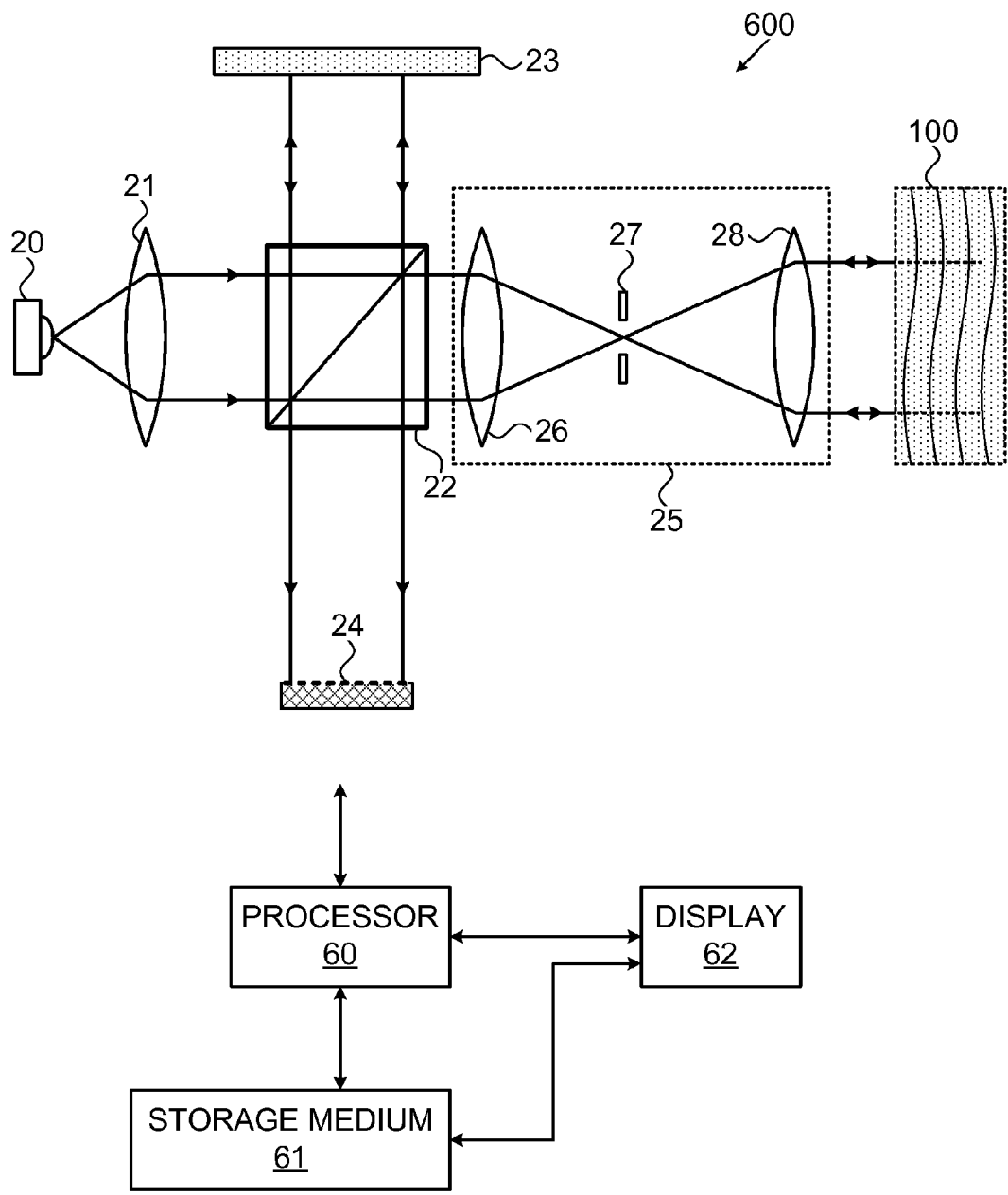
FIG. 6 is a schematic illustration of a full-field OCT system for acquiring images from within a tissue, in accordance with a third embodiment of the present invention.

Reference is now made to FIG. 6, which illustrates a schematic full-field OCT system 600 for acquiring images from within a tissue, in accordance with a third embodiment of the present invention. The OCT system 600 disclosed in FIG. 6 may comprise illumination source 20. Illumination source 20 may typically illuminate light in relatively long wavelength, e.g., near-infrared light, which penetrates into inner layers of a tissue target. Illumination source 20 may be a tunable illumination source that may illuminate in variable frequencies or wavelengths of light, e.g., a tunable laser, or a monochromator, which illuminates light in changing monochromatic wavelengths within the range of near-infrared light. Illumination source 20 may operate automatically such that it may change the frequency/wavelength of illumination according to a predetermined and preprogrammed timeline. In other embodiments, the operation of illumination source 20 may be controlled in real time by an operator of the OCT system 600. Tunable illumination source 20 eliminates the need for a moveable reference mirror. The scanning along z axis, i.e., into the deeper layers of tissue 100, which may be achieved by moving reference mirror 23, as described in systems 300 and 400 (FIGS. 3 and 4, respectively), may be achieved in system 600 by using a tunable illumination source, such that each wavelength of light correlates to a different depth of tissue layer.

Illuminations source 20 may be designed such to create a relatively large illumination beam area compared to that of illumination sources used in prior art OCT systems, which create a thin single pixel pencil beam. For example, the illumination beam area may be 1 $mm^2$ or 5 $mm^2$, though other sizes of the beam may be possible. The illumination beam area is large such that there is congruence between the field of illumination (FOI) and the field of view (FOV). Thus, OCT system 600 eliminates the need for transverse scanning that is required in prior art systems, since in one illumination session of system 600, the entire image is captured.

The OCT system 600 may further comprise a collimator 21, for collimating the illuminated light rays irradiated by illumination source 20. The collimated light rays may then be split by beam splitter 22; some of the collimated light rays may be directed towards a reference mirror 23, which is a static mirror (unlike the moveable reference mirror described in FIGS. 3 and 4), and some of the collimated rays may be directed towards the tissue target 100. The light rays that reach reference mirror 23 may be reflected off it towards imager 24, through beam splitter 22. In some embodiments, beam splitter 22, static reference mirror 23, and imager 24 may compose an interferometer, e.g., a Michelson interferometer.

Telecentric optical system 25 may be located between beam splitter 22 and tissue target 100. In some embodiments, telecentric optical system 25 may comprise a collimating/condensing lens 26, an aperture 27 and condensing/collimating lens 28. Before light rays that are reflected off the tissue, reach imager 24, they pass through telecentric optical system 25. The light rays reflected off the tissue pass through condensing/collimating lens 28, which condenses the light rays and enables some of them to pass through aperture 27. The rays that passed through aperture 27 may then pass through collimating/condensing lens 26, which filters the light rays such that only collimated light rays that are parallel to originally illuminated collimated light rays may pass through collimating/condensing lens 26, while the rest of the rays do not pass through collimating/condensing lens 26. The result is that imager 24 may only collect light rays that are reflected by the tissue parallel to originally collimated light rays, thus substantially no noise reaches imager 24.

Only light rays that are parallel to the collimated illuminated light rays are needed to be compared to the light rays reflected off reference mirror 23 in order to acquire a meaningful signal. Since the light rays reflected off reference mirror 23 are collimated (since a mirror reflects light rays off it in the same direction that light rays are illuminated onto it), in order to be able to compare the signal reflected off reference mirror 23 to the signal reflected off the tissue, the signals should be of the same direction. Light rays reflected off the tissue at other directions are considered noise, since they cannot be compared to the signal reflected off reference mirror 23.

In some embodiments, the optical axes of static reference mirror 23 and imager 24 may be perpendicular to the optical axis of collimated light from illumination source 20 and to collimated light reflected off tissue 100.

In some embodiments, telecentric optical system 25 may be located between imager 24 and beam splitter 22, instead of between tissue 100 and beam splitter 22. In this embodiment, the light rays that are reflected off tissue 100 first pass through beam splitter 22 in order to be directed towards imager 24. However, before the light rays are being collected by imager 24, the light rays may be filtered by telecentric optical system 25 such that only collimated light rays reach imager 24.

Imager 24 may create an interference pattern per every frequency/wavelength of illumination. The collimated light rays reflected off reference mirror 23, and the collimated light rays reflected off tissue target 100 create the interference pattern image. The image of interference pattern created by imager 24 may provide the interference pattern for a certain monochromatic wavelength.

For every illumination wavelength $\lambda_1 \ldots \lambda_n$ (illuminated by illumination source 20 within a predetermined range), an interference pattern may be acquired by imager 24. That is, the intensity of light acquired by imager 24 per each illumination frequency/wavelength $\lambda_i$ may be recorded, such that the number of images acquired by imager 24 is equivalent to the number of monochromatic wavelengths illuminated by illumination source 20. System 600 may comprise a processor or controller 60 that may apply Fast Fourier Transform (FFT) on the intensity of light acquired per pixel $(x_i, y_j)$ of imager 24 for each of the entire illumination frequencies/wavelengths $(\lambda_1 \ldots \lambda_n)$. By applying FFT on each of the illumination frequencies per pixel, the changes in reflectivity in a certain point in a layer $(z_i)$ along the tissue that corresponds to pixel $(x_i, y_j)$, may be detected. Changes in reflectivity of the tissue may indicate on presence of a foreign body (e.g., polyp) along or within the tissue. Following the Fourier transform, new images may be created by processor 60, incorporating the FFT results. Each pixel $(x_i, y_j)$ correlates with a plurality of tissue layers, since a plurality of images are acquired for a plurality of illumination frequencies. Processor 60 may then combine all pixels correlated with the same tissue layer $(z_i)$ in order to create a full two dimensional image per each tissue layer. All of the pixels $(x_1, y_1)$ to $(x_m, y_m)$ per each tissue layer $(z_i)$ may create new images illustrating the tissue characteristics (e.g., by changes in tissue reflectivity) per each tissue layer. The new images correlate between light intensity and the tissue layer $(z_i)$ instead of correlating between light intensity and illuminated frequency as in the originally acquired images.

According to some embodiments, system 600 in FIG. 6 may further comprise a display unit 62. Display unit 62 may either display the two dimensional images as slices positioned one aside the other or as a complete three-dimensional view of the tissue target by overlaying the images one on top of the other.

According to some embodiments, system 600 may further comprise an article such as a computer or processor readable non-transitory storage medium 61, such as for example a memory, a disk drive, or a USB flash memory device encoding, including or storing instructions, e.g., computer-executable instructions, which when executed by processor or controller 60, may cause processor or controller 60 to carry out methods disclosed herein.

Figure 7:
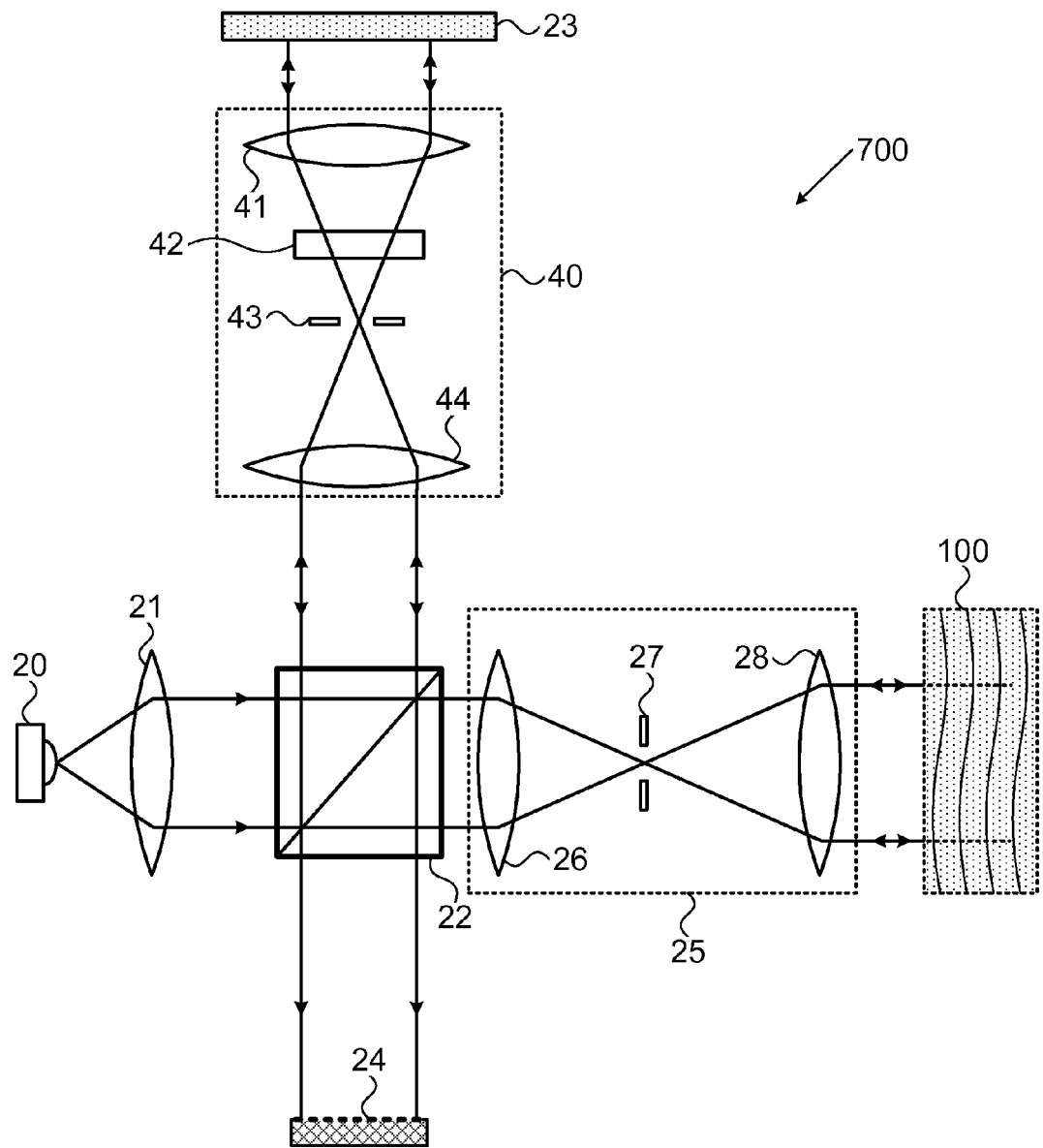
FIG. 7 is a schematic illustration of a full-field OCT system for acquiring images from within a tissue, in accordance with a fourth embodiment of the present invention.

Reference is now made to FIG. 7, which schematically illustrates a full-field OCT system 700 for acquiring images from within a tissue, in accordance with a fourth embodiment of the present invention. OCT system 700 in FIG. 7 may comprise a first telecentric optical system 25, as in system 600 of FIG. 6, and a second telecentric optical system 40. This second telecentric optical system 40 may be located between reference mirror 23 and beam splitter 22. Telecentric optical system 40 may comprise an arrangement of lenses, e.g., condensing/collimating lens 41, a shutter 43, and a collimating/condensing lens 44.

Since telecentric optical system 25 decreases the amount of light rays reflected off the tissue and which reach imager 24 by filtering out non-collimated light rays, the intensity of light rays detected from tissue 100 by imager 24 is quite low. Therefore, in order to enable imager 24 to create an image from the light rays reflected off tissue 100, the illumination source 20 should typically be of high intensity. A high intensity illumination source 20 may cause light rays reflected off reference mirror 23 to be of high intensity as well. When the intensity of light reflected off mirror 23 is higher than the intensity of light reflected off the tissue, comparing the intensity of light rays reflected by tissue 100 to the intensity of light rays reflected by reference mirror 23 is quite difficult (as described in details with regards to FIG. 4).

Therefore, telecentric optical system 40 may be used in order to decrease the amount of light that is reflected off reference mirror 23, thus decreasing the intensity of light reflected off reference mirror 23. According to some embodiments, light rays reflected off reference mirror 23 may pass through condensing/collimating lens 41, and may then pass through shutter 43. Shutter 43 may limit the amount of rays that pass through it, thus decreasing the intensity of light reflected off reference mirror 23. The light rays that did pass through shutter 43 may then pass through collimating/condensing lens 44 in order to conform to the direction of initially illuminated collimated light rays, and thus serve as a reference (of both intensity and direction) to the collimated light rays reflected off tissue target 100.

According to some embodiments, shutter 43 may be changeable, such that it may be synchronized with the changing tissue depth from which images are acquired. Illumination source 20 may be a tunable illumination source, in order to enable image acquisition from various depths within the tissue, such that the overall changing illumination frequencies, i.e., wavelengths, may be transformed by Fast Fourier Transform to the overall various depths within the tissue. The deeper the layer is within the tissue, the less light rays reflected off the tissue reach imager 24. Therefore, shutter 43 should be adjusted according to the depth within the tissue from which images are acquired. The deeper the layer is, the smaller the opening of shutter 43 is, and vice versa. In some embodiments, changing the wavelengths that illumination source 20 illuminates, as well as changing the opening/closure of shutter 43 may be manually performed by an operator of OCT system 400. In other embodiments, changes of the wavelengths that illumination source 20 illuminates and the synchronized opening/closure of shutter 43 may be performed automatically such that images of different illumination wavelengths may automatically be acquired one after the other. The wavelength of light illuminated by illumination source 20 and thus amount of opening/closure of shutter 43 may be preset by the operator of OCT system 400, according to embodiments of the present invention.

In some embodiments, telecentric optical system 40 may comprise a neutral density filter 42, which may be located between condensing/collimating lens 41 and collimating/condensing lens 44. Neutral density filter 42 may replace, or be added to shutter 43. Neutral density filter 42 may be a variable uniform density filter, which may decrease the intensity of light reflected off reference mirror 23. In some embodiments, a set of discrete filters may be used so that a desired filter is positioned between condensing/collimating lens 41 and collimating/condensing lens 44. The filters may synchronously change with the changing wavelengths of tunable illumination source 20 and thus decrease the intensity of light reflected off mirror 23 in the appropriate amount that corresponds to the intensity of light reflected off tissue target 100. For example, the set of filters may be arranged on a wheel turnable in a plane perpendicular to the optical axis of telecentric optical system 25, such that a desired filter may be positioned in the path of light between condensing/collimating lens 41 and collimating/condensing lens 44.

In other embodiments, reducing the intensity of illumination of light reflected off reference mirror 23 may be achieved by incorporating into the system a non-symmetrical beam splitter, instead of beam splitter 22. A non-symmetrical beam splitter may only deliver towards reference mirror 23 a fraction of the illumination that is delivered towards tissue 100.

Figure 8:
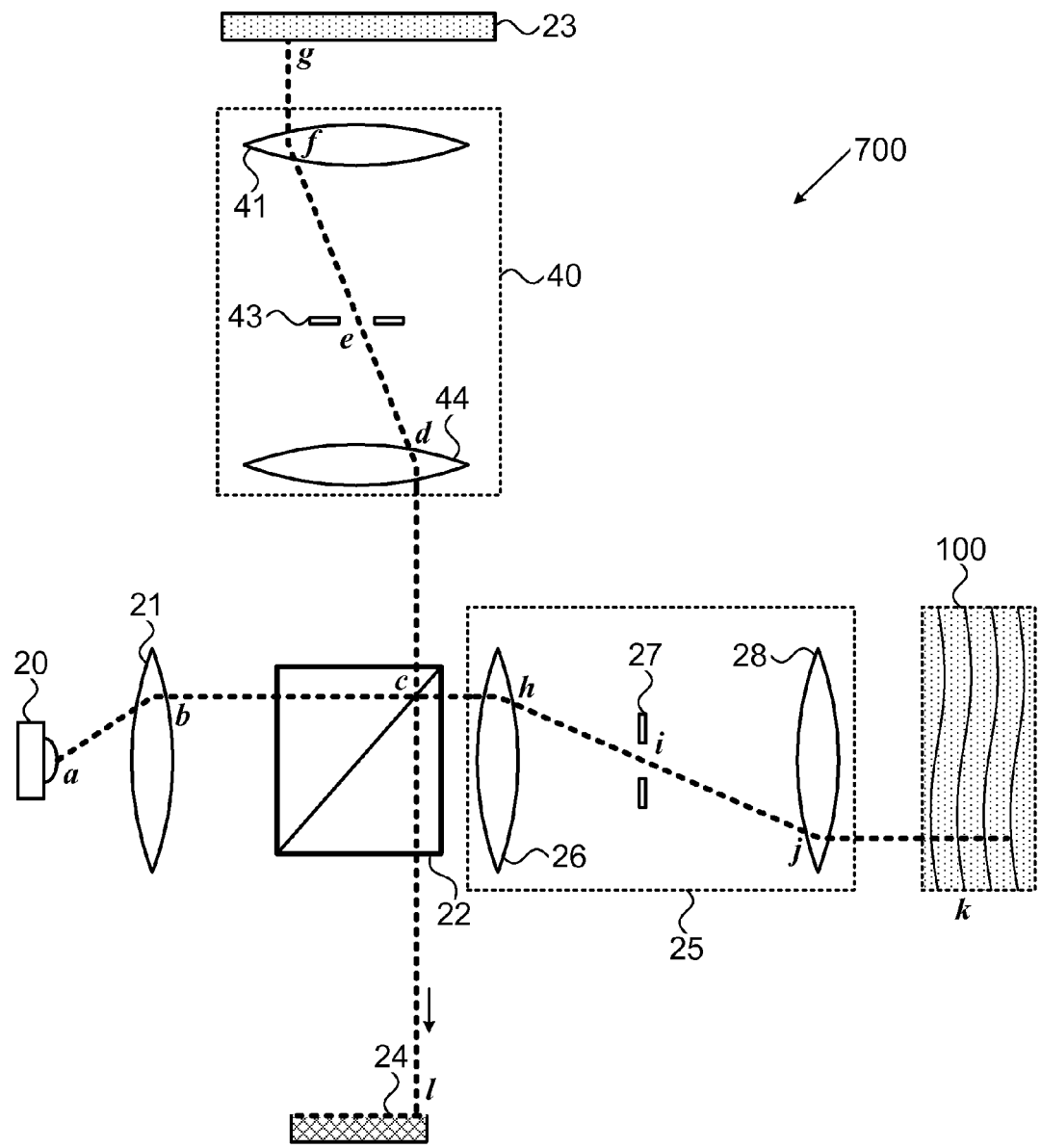
FIG. 8 is a schematic illustration of the path of light rays from the illumination source to the imager, in accordance with embodiments of the present invention.

Reference is now made to FIG. 8, which schematically illustrates the path of light rays from the illumination source to the imager, in accordance with embodiments of the present invention. According to some embodiments, the path of light rays that are reflected off reference mirror 23 may be as follows: light rays are illuminated from tunable illumination source 20 (*a*), pass through collimator 21 (*b*), and reach beam splitter 22 (*c*). The rays are split and some are reflected towards reference mirror 23; condensed by collimating/condensing lens 44 (*d*), past shutter 43 (*e*) and collimated by condensing/collimating lens 41 (*f*). Then the rays are reflected off mirror 23 (*g*), condensed by condensing/collimating lens 41 (*f*), past shutter 43 (*e*) and collimated by collimating/condensing lens 44 (*d*), in order to decrease intensity of light and to allow passage of collimated rays only. The rays may then pass through beam splitter 22 (*c*), and may be detected by imager 24 (*l*).

According to some embodiments, the path of light rays reflected off the tissue target may be as follows: light rays are illuminated from tunable illumination source 20 (*a*), pass through collimator 21 (*b*), and reach beam splitter 22 (*c*). The rays are split and some of the rays that are not reflected towards reference mirror 23 are reflected towards tissue 100. The rays reflected towards tissue 100 may be condensed by collimating/condensing lens 26 (*h*), pass through shutter 27 (*i*) and may be collimated by condensing/collimating lens 28 (*j*). Then the light rays may be reflected off tissue 100 (*k*), may be condensed by condensing/collimating lens 28 (*j*), past shutter 27 (*i*), and collimated by collimating/condensing lens 26 (*h*), in order to allow passage of collimated rays alone. The rays may then pass through beam splitter 22 (*c*) and may be detected by imager 24 (*l*).

Figure 9A:
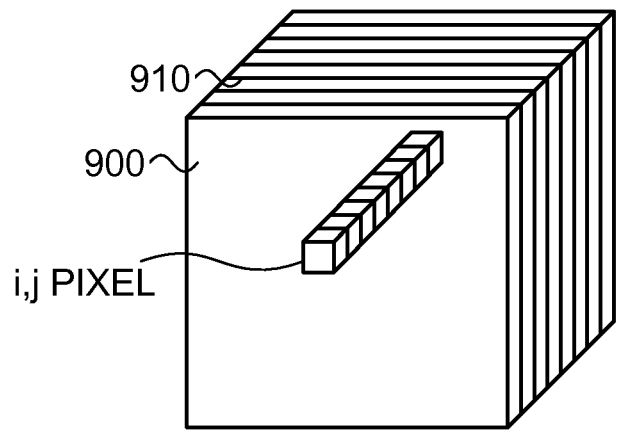
FIGS. 9A-B are schematic illustrations of an image display, in accordance with embodiments of the present invention.
Figure 9B:
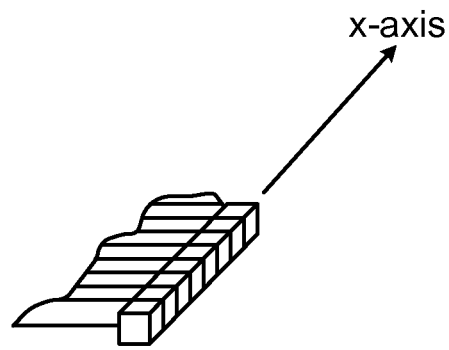

Reference is now made to FIGS. 9A-B, which schematically illustrate an image display, in accordance with embodiments of the present invention. FIG. 9A illustrates an image display of full 2D images for every tissue layer of, for example, tissue 100 (FIG. 6, FIG. 7). These images comprise an image 900 of the tissue surface, and images of inner layers, e.g., images 910. Images 910 may be created per each tissue layer following FFT being applied onto the originally acquired images. The FFT is applied per imager's pixel for the entire wavelengths illuminated onto the tissue, and thereby transforms the illumination frequency to tissue depth. The new images are created by combining all pixels that correlate to the same depth of the same tissue layer.

One possible image display includes displaying the images side by side, beginning with the most superficial layer on the left (e.g., image 900) and ending with the deepest layer on the right, or vice versa. Another possible display, as shown in FIG. 9A, includes overlaying the images one on top of the other, so as to create a 3D image of the tissue. According to FIG. 9B, an operator may select a section of the 3D image that seems suspicious for expressing pathologies, e.g., a polyp, and may examine that section along the entire tissue layers, thereby being able to better assess the tissue condition.

Figure 10:
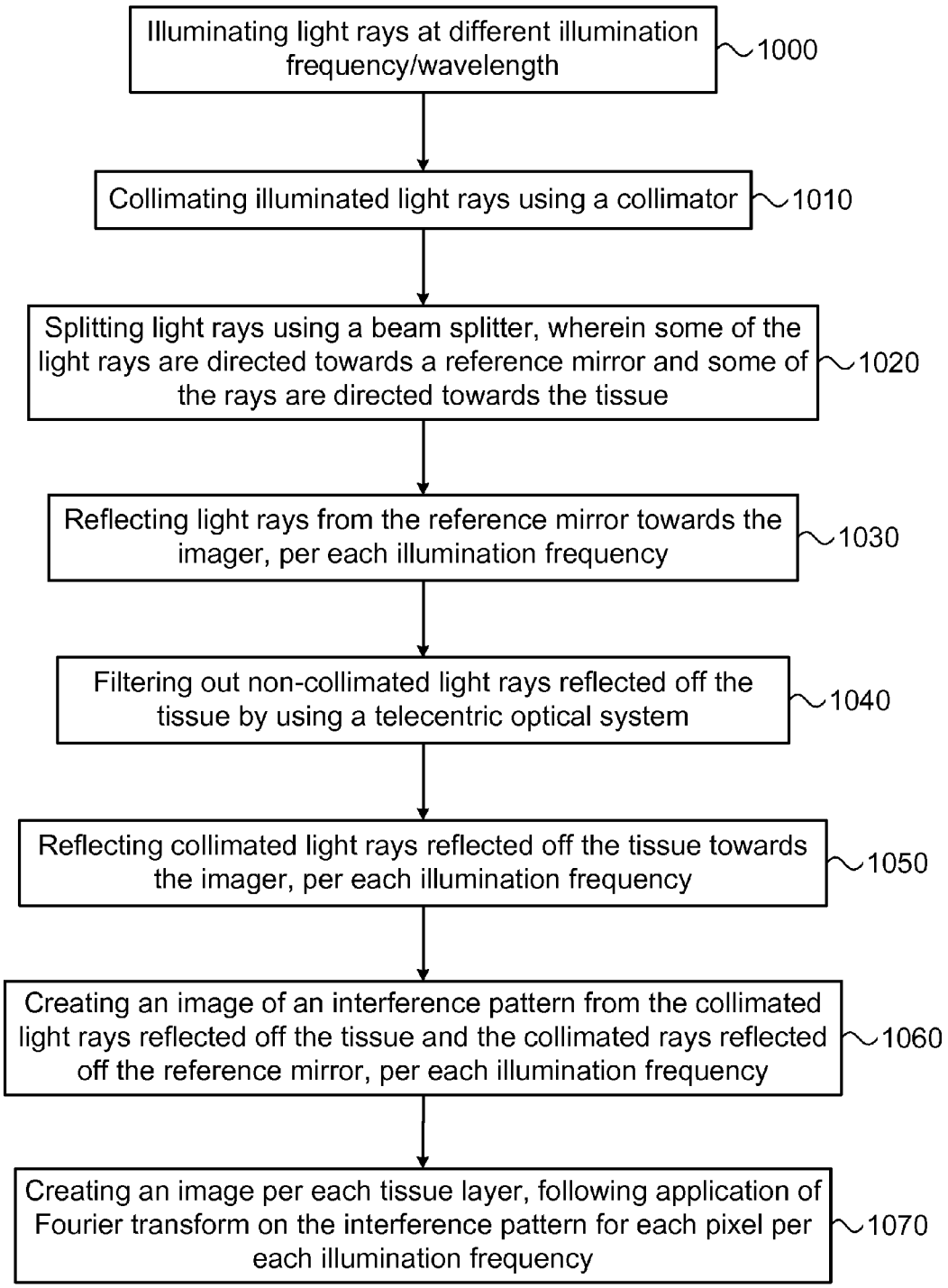
FIG. 10 is a flow chart illustrating a method for acquiring and processing images from within a tissue, in accordance with embodiments of the present invention.

Reference is now made to FIG. 10, which illustrates a flow chart of a method for acquiring and processing images from within depth layers of a tissue, in accordance with embodiments of the present invention. The method may comprise the following steps:

illuminating light rays at different changing illumination frequency/wavelength onto a tissue (1000);

collimating illuminated light rays using a collimator (1010);

splitting light rays using a beam splitter, wherein some of the light rays are directed towards a reference mirror and some of the rays are directed towards the tissue, while both portions of light rays preserve their collimated nature (1020);

reflecting light rays from the reference mirror towards the imager, per each illumination frequency (1030);

filtering out non-collimated light rays reflected off the tissue by using a telecentric optical system (1040);

reflecting collimated light rays reflected off the tissue towards the imager, per each illumination frequency (1050);

creating an image of an interference pattern from the collimated light rays reflected off the tissue and the collimated light rays reflected off the reference mirror, per each illumination frequency (1060); and creating a full 2D image per each tissue layer, following application of Fourier transform on the interference pattern for each pixel per each illumination frequency (1070).

According to some embodiments, the method may further comprise the step of decreasing intensity of light reflected off the reference mirror (synchronously with changing frequency of illuminated light) by using a second telecentric optical system (for example, telecentric optical system 40, in FIG. 7). The step of decreasing intensity of light reflected off the reference mirror may be performed prior to reflecting light rays from the reference mirror towards the imager (1030).

According to some embodiments, the step of filtering out non-collimated light rays reflected off the tissue may be performed subsequent to the step of reflecting collimated light rays reflected off the tissue towards the imager, as the telecentric optical system may be located between the beam splitter and the imager (instead of between the beam splitter and the tissue).

In some embodiments, the method may further comprise the step of comparing the full 2D images to images of various pathologies. Comparison between the acquired 2D images and various pathologies may enable assessment of the condition of the imaged tissue, e.g., whether the tissue comprises any of the reference pathologies or whether the imaged tissue is healthy.

Figure 11:
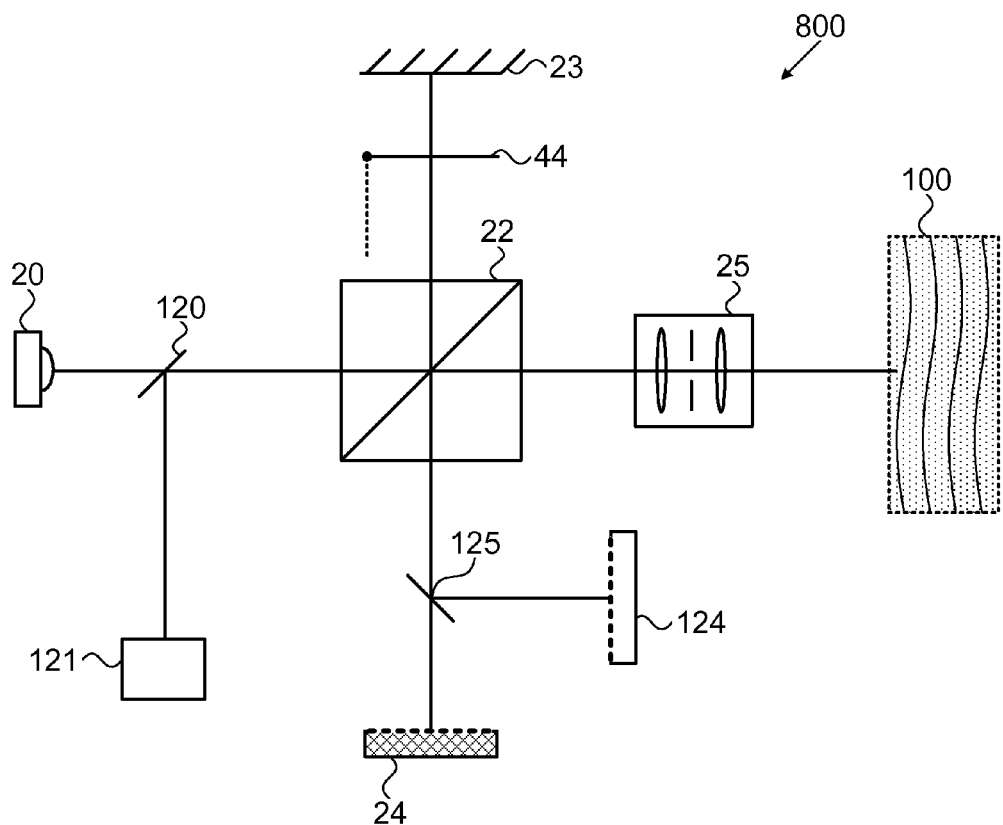
FIG. 11 is a schematic illustration of a full-field OCT system for acquiring images from within a tissue as well as acquiring white light images of the surface of the tissue, in accordance with embodiments of the present invention.

Reference is now made to FIG. 11, which is a schematic illustration of a full-field OCT system for acquiring images from within a tissue as well as acquiring white light images of the surface of the tissue, in accordance with embodiments of the present invention. FIG. 11 illustrates OCT system 800, which incorporates an OCT system similar to the systems described in FIGS. 6 and 7, while further incorporating a white light illumination source 121 and a white light/color imager 124. Once system 800 is operated, it may first acquire a white light image using white light illumination source 121 for illuminating tissue 100, and collecting the light reflected off tissue 100 by white light imager 124. White light rays from illumination source 121 may be reflected by beam splitter 120 onto beam splitter 22 and towards tissue 100. During this process, shutter 44 may block passage of light towards reference mirror 23. Next, white light illumination source 121 may be shut off and illumination source 20 may begin illuminating in order to begin the procedure of creating OCT depth images of tissue 100. During operation of illumination source 20 shutter 44 may be opened to enable passage of light rays towards reference mirror 23 and from it towards imager 24. Further, during operation of illumination source 20, the route leading light rays towards white light imager 124 may be blocked by beam splitter 125, and thus light rays may only be reflected towards imager 24 from both tissue 100 and reference mirror 23.

The white light image created by imager 124 may then be processed such that it is superimposed onto the OCT images of the tissue layers. This may enable a display of a color image as the most superficial layer of the tissue, while the internal layers are in grey level, i.e., monochromatic.

Figure 12:
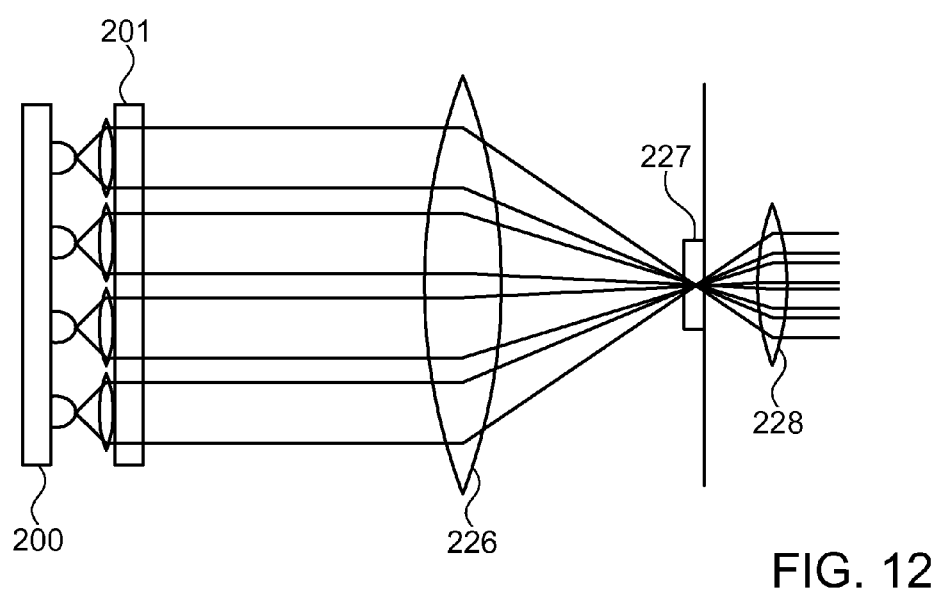
FIG. 12 is a schematic illustration of an illuminator that is part of a full-field OCT system, in accordance with an embodiment of the present invention.

Reference is now made to FIG. 12, which is a schematic illustration of an illumination that is part of a full-field OCT system, in accordance with an embodiment of the present invention. The illuminator illustrated in FIG. 8 may replace the illumination sources 20 in either FIG. 6 or FIG. 7. That is, the illuminator in FIG. 12 may be placed in a full-field OCT system next to the beam splitter. The illuminator may comprise a plurality of illumination sources 200. In some embodiments, each of illumination sources 200 illuminates at a different phase, such that illumination sources 200 are not coherent in time. Light rays irradiated from each of illumination sources 200 may be collimated by collimating lens array 201. The light rays may then be collected by collecting or condensing lens 226, such that they may pass through pin hole 227, which comprises a diffusing glass acting as a mask for mixing the rays to get the effect of a high intensity illumination source. The light rays may then pass through another collimating lens 228 for collimating the light rays onto the beam splitter, e.g., beam splitter 22 in FIG. 6 or FIG. 7.

There are a few advantages in using more than one illumination source as part of an OCT system. One advantage is that a plurality of illumination sources may provide higher intensity of light illuminated towards the tissue, which may increase the chances of light to penetrate deep layers as well as superficial layers. Thus, collection of data on a number of deep tissue layers as well as collection of data on superficial tissue layers may be enabled. Another advantage of using more than one illumination source that have low coherence in time, is that low coherence of illumination sources leads to better resolution of the images acquired from light reflected off the tissue. When the illumination sources used to illuminate the tissue are not coherent, comparison between the reference image acquired from light reflected off the reference mirror, and the image acquired from light reflected off the tissue, would provide a more accurate indication on the specific tissue layer which light was reflected from. The more non-coherent illumination sources used, the better the image resolution.

Any of the described OCT systems of the invention may be miniaturized and incorporated into an endoscope or a swallowable capsule endoscope, in order to create 2D and/or 3D images of the gastrointestinal lumen.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:
1. A system for acquiring images from within depth layers of a tissue, said system comprising:
    an illumination source for illuminating a tissue, wherein said illumination source illuminates a large illumination beam area;
    a collimator for collimating the light from the illumination source;
    an interferometer comprising:
        a beam splitter located between the illumination source and the tissue;
        a moveable reference mirror; and
        an imager,
        wherein optical axes of said moveable mirror and said imager are perpendicular to the optical axis of collimated light from said illumination source and to collimated light from said tissue, and wherein said beam splitter is located between said moveable mirror and said imager; and
    a first telecentric optical system for passing through only collimated reflected light, said first telecentric optical system located between the beam splitter and the tissue;
    a second telecentric optical system configured to decrease intensity of light reflected off the reference mirror synchronously with movement of the reference mirror, said second telecentric optical system located between the beam splitter and the reference mirror, wherein said second telecentric optical system comprises a collimating lens, a shutter and a condensing lens,
wherein said imager is configured to generate an interference pattern for each depth layer of the tissue, according to the collimated reflected light.

2. The system according to claim 1, wherein said first telecentric optical system comprises a collimating lens, a shutter and a condensing lens.

3. The system according to claim 1, wherein said illumination source illuminates at near-infrared wavelength.

4. The system according to claim 1, wherein said interferometer is a Michelson interferometer.

5. The system according to claim 1, wherein said system further comprises a processor configured to generate slices or a complete three-dimensional view of the tissue from said interference patterns generated by the imager.

6. A method for acquiring images from within depth layers of a tissue, said method comprising the steps of:
illuminating light rays with large illumination beam area;
collimating illuminated light rays using a collimator;
splitting light rays using a beam splitter, wherein some of the light rays are directed towards a reference mirror and some of the rays are directed towards the tissue;
reflecting light rays from the reference mirror towards the imager;
moving the reference mirror in order to obtain images of various depths from within the tissue;
filtering out non-collimated light rays reflected off the tissue by using a first telecentric optical system;
reflecting collimated light rays reflected off the tissue towards the imager;
decreasing intensity of light reflected off the reference mirror synchronously with the movement of the reference mirror by using a second telecentric optical system;
creating an image of an interference pattern from the collimated light rays reflected off the tissue and the collimated light rays reflected off the reference mirror.

7. The method according to claim 6, wherein the method further comprises the step of creating an image of an interference pattern for each depth layer, from the collimated light rays reflected off the tissue.

8. The method according to claim 6, wherein the method further comprises the step of comparing the interference image to images of various pathological tissues.

9. A system for acquiring images from within depth layers of a tissue, said system comprising:
a monochromator illumination source for illuminating a large illumination beam area of the tissue with different changing monochromatic frequencies of light;
a collimator for collimating the light from the illumination source;
an interferometer comprising:
a beam splitter located between the illumination source and the tissue;
a static reference mirror;
an imager, and
a processor,
wherein optical axes of said mirror and said imager are perpendicular to the optical axis of collimated light from said illumination source and to collimated light from said tissue, and wherein said beam splitter is located between said minor and said imager; and
a first telecentric optical system for passing through only collimated reflected light, said first telecentric optical system located between the beam splitter and the tissue;
a second telecentric optical system configured to decrease intensity of light reflected off the reference mirror synchronously with changing frequency of illuminated light, said second telecentric optical system located between the beam splitter and the reference mirror, wherein said second telecentric optical system comprises a collimating lens, a shutter and a condensing lens,
wherein said imager is configured to generate interference pattern images per each different illumination frequency, and wherein said processor is configured to process said images by a Fast Fourier Transform to images illustrating tissue characteristics per each depth of tissue layer.

10. The system according to claim 9, wherein said first telecentric optical system comprises a collimating/condensing lens, a shutter and a condensing/collimating lens.

11. The system according to claim 9, wherein said illumination source illuminates light at different changing wavelengths within a range of near-infrared light.

12. The system according to claim 9, wherein said interferometer is a Michelson interferometer.

13. The system according to claim 9, wherein said processor generates slices or a complete three-dimensional view of the tissue from said processed images.

14. A method for acquiring images from within depth layers of a tissue, said method comprising the steps of:
illuminating light rays at different changing illumination frequency onto a tissue;
collimating illuminated light rays using a collimator;
splitting light rays using a beam splitter, wherein some of the light rays are directed towards a reference mirror and some of the rays are directed towards the tissue;
reflecting light rays from the reference mirror towards the imager, per each illumination frequency;
filtering out non-collimated light rays reflected off the tissue by using a first telecentric optical system;
reflecting collimated light rays reflected off the tissue towards the imager, per each illumination frequency;
decreasing intensity of light reflected off the reference mirror, synchronously with changing frequency of illuminated light, by using a second telecentric optical system;
creating an image of an interference pattern from the collimated light rays reflected off the tissue and the collimated light rays reflected off the reference mirror, per each illumination frequency; and
creating a full 2D image per each tissue layer, following application of Fourier transform on the interference pattern for each pixel per each illumination frequency.

15. The method according to claim 14, wherein the method further comprises the step of comparing the full 2D image to images of various pathologies.

* * * * *